United States Patent [19]

Grollier et al.

[11] Patent Number: 5,063,052
[45] Date of Patent: Nov. 5, 1991

[54] COSMETIC AND DERMATOLOGICAL APPLICATION OF POLYSILOXANES CONTAINING A DIESTER FUNCTIONAL GROUP AND COMPOSITIONS EMPLOYED

[75] Inventors: Jean F. Grollier, Paris; Claude Dubief, Le Chesnay, both of France

[73] Assignee: L'Oreal, Paris, France

[21] Appl. No.: 412,788

[22] Filed: Sep. 26, 1989

[30] Foreign Application Priority Data

Sep. 28, 1988 [LU] Luxembourg ............................ 87350

[51] Int. Cl.$^5$ .............................................. A61K 7/06
[52] U.S. Cl. ........................................ 424/70; 424/47; 514/844; 514/880; 556/417; 556/419; 528/15; 526/932; 252/78.3; 252/39; 428/391
[58] Field of Search ............... 556/417, 419; 252/78.3, 252/39; 528/15; 526/932; 424/70, 47; 514/844, 880; 428/391

[56] References Cited

U.S. PATENT DOCUMENTS

| | | | |
|---|---|---|---|
| 4,166,078 | 8/1979 | Getson | 556/417 |
| 4,207,246 | 6/1980 | Hafner | 252/78.3 |
| 4,609,750 | 9/1986 | Kollmeier | 556/419 |
| 4,699,813 | 10/1987 | Cavenzzan | 528/15 |
| 4,741,966 | 5/1988 | Cavenzzan | 528/15 |
| 4,839,166 | 6/1989 | Grollier | 526/932 |
| 4,844,888 | 7/1989 | Zawadzki | 424/70 |
| 4,851,521 | 7/1989 | della Valle et al. | 514/844 |
| 4,853,430 | 8/1989 | Stühler et al. | 514/844 |
| 4,898,725 | 2/1990 | Hoeffkes et al. | 424/70 |
| 4,925,659 | 5/1990 | Grollier | 514/880 |

FOREIGN PATENT DOCUMENTS 0004074 9/1979 European Pat. Off. .
0186438 7/1986 European Pat. Off. .

*Primary Examiner*—Thurman K. Page
*Assistant Examiner*—William E. Benston, Jr.
*Attorney, Agent, or Firm*—Marshall, O'Toole, Gerstein, Murray & Bicknell

[57] ABSTRACT

Cosmetic and dermatological application of polysiloxanes containing a diester functional group and compositions employed.

The invention relates to the use in cosmetics and in dermatology of diorganopolysiloxanes containing a diester functional group carrying, per molecule, at least one unit of formula:

$$ZR_aSiO_{(3-a)/2}$$

where a is 0, 1 or 2, Z is a radical of formula:

$$W-\underset{\underset{X}{|}}{\overset{\overset{COOR'}{|}}{C}}-CH_2-COOR'$$

the symbols R', which are identical or different, denote a $C_1$–$C_{12}$ monovalent saturated hydrocarbon, $C_2$–$C_{12}$ alkoxyalkyl or $C_8$–$C_{12}$ aryl, alkylaryl or aralkyl radical, X denotes H or $CH_3$; W is a covalent bond or a $C_1$–$C_4$ alkylene radical; and the symbols R, which are identical or different, denote $C_1$–$C_{20}$ alkyl, vinyl, phenyl, 3,3,3-trifluoropropyl or hydroxyl, provided that only one radical R per silicon atom denotes hydroxyl.

21 Claims, No Drawings

COSMETIC AND DERMATOLOGICAL APPLICATION OF POLYSILOXANES CONTAINING A DIESTER FUNCTIONAL GROUP AND COMPOSITIONS EMPLOYED

Cosmetic and dermatological application of polysiloxanes containing a diester functional group and compositions employed.

The present invention relates to the cosmetic and dermatological use of diorganopolysiloxanes containing a diester functional group, to the cosmetic and dermatological compositions employed and to the cosmetic treatment process, in particular of hair and of the skin.

Silicone oils are already employed in cosmetics as a lubricant in compositions intended for the treatment and care of hair and of the skin. They are chiefly polydimethylsiloxanes.

The applicant has found, surprisingly, that the use of silicone oils consisting of diorganopolysiloxanes containing a diester functional group made it possible to obtain shining, soft air which disentangled easily, while having a non-greasy feel. These compounds also have the advantage of imparting softness and a nonsticky feel to the skin.

A 'cosmetic treatment' is the name given to a treatment intended to obtain one or more of the results indicated above on hair. The same applies to the cosmetic treatment of the skin.

A subject of the invention consists, therefore, of the cosmetic and dermatological use of diorganopolysiloxanes containing a diester functional group.

Another subject of the invention is a process of cosmetic treatment of hair or of the skin employing these compounds.

Another subject of the invention consists of the cosmetic and dermatological compositions intended for the treatment of the skin or of hair, employing these compounds.

Further subjects of the invention will become apparent on reading the description and the examples which follow.

The principal subject of the present invention is therefore the cosmetic and dermatological use of diorganopolysiloxanes containing a diester functional group, carrying, per molecule, at least one unit of formula:

$$ZR_aSiO_{(3-a)/2} \tag{I}$$

in which:
a is 0, 1 or 2
Z is chosen from the radicals of formula:

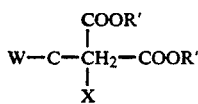

in which:
the symbols R', which are identical or different, denote a $C_1$-$C_{12}$ monovalent saturated hydrocarbon radical, a $C_2$-$C_{12}$ monovalent alkoxyalkyl radical or a $C_6$-$C_{12}$ aryl, alkylaryl or aralkyl radical;

X denotes a hydrogen atom or a methyl radical;

W denotes a covalent bond or a $C_1$-$C_4$ linear or branched alkylene radical;

the symbols R, which are identical or different, denote a $C_1$-$C_{20}$ alkyl, vinyl, phenyl, 3,3,3-trifluoropropyl or hydroxyl radical, provided that only one of the radicals R per silicon atom may be a hydroxyl;

or a mixture of these compounds.

The other siloxy units of the organopolysiloxane correspond to the formula:

$$R_bSiO_{(6-b)/2} \tag{I bis}$$

in which:
R has the same meaning as above; and
b is equal to 0, 1, 2 or 3.

When X denotes a hydrogen atom, the preferred alkylene groups W are chosen from the following radicals:

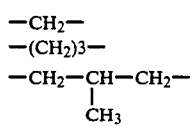

When the group W is a single covalent bond, X preferably denotes a methyl group.

R' preferably denotes a $C_1$-$C_{12}$ alkyl radical chosen in particular from methyl, ethyl, n-propyl, isopropyl, n-butyl, 2-ethylhexyl, heptyl and dodecyl radicals.

The preferred $C_6$-$C_{12}$ aryl, arylalkyl and alkylaryl radicals denoted by R' are chosen from phenyl, benzyl and tolyl radicals.

The preferred $C_2$-$C_{12}$ alkoxyalkyl radicals denoted by R', according to the invention, are methoxymethyl, ethoxymethyl and 2-methoxyethyl groups.

The preferred alkyl radicals R, in accordance with the invention, are methyl, ethyl, propyl, n-butyl, n-octyl and 2-ethylhexyl.

At least 80% of the number of the radicals R in the compounds in accordance with the invention are preferably methyl.

The compounds which are more particularly preferred, according to the invention, are the cyclic or linear polymers chosen from:

(i) the polysiloxanes corresponding to the formula:

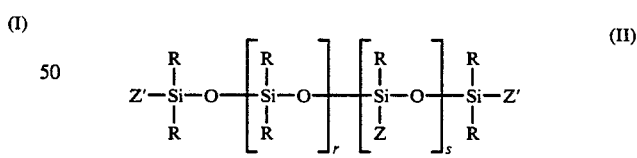

in which:
R has the same meaning as that given above;
the symbols Z', which are identical or different, are chosen from R and Z;
Z has the same meaning as that shown above and is preferably chosen from the radicals
CH₂CH(COOR')CH₂COOR'
C(CH₃) (COOR')CH₂COOR'
R' having the same meanings as defined above;
r is an integer between 0 and 500 inclusive;
s is an integer chosen between 0 and 50 inclusive; and
if s is 0, at least one of the two symbols Z' is Z;
(ii) the cyclic polysiloxanes of formula

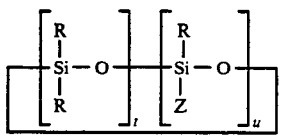  (III)

in which:

R and Z have the same meaning as above;
u is an integer between 1 and 20 inclusive; and
t is an integer between 0 and 20 inclusive;
t+u is greater than or equal to 3.

Preference is given more particularly to random or block polymers of formulae (I), (II) and (III), exhibiting at least one of the following characteristics:

R and R' are methyl
r is between 5 and 50 inclusive
s is between 1 and 20 inclusive
t+u is between 3 and 10 inclusive.

The polymers according to the invention may be prepared in particular according to a first process (A).

During a first stage ($A_1$), an organic diester of formula:

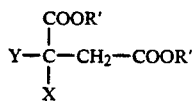  (IV)

or of formula:

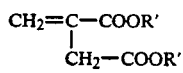  (IV bis)

Y being chosen from a linear or branched alkenyl group containing from 2 to 4 carbon atoms inclusive;
R' and X having the same meaning as in formula (I), is added to a hydroorganosilane of formula:

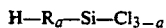  (V)

R and a having the same meaning as in formula (I) above.

This gives an additional product of formula:

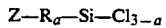  (VI)

in which R, Z and a have the same meaning as in formula (I) above.

Stage ($A_1$) may be performed in bulk or in solution in an organic solvent.

The reaction is exothermic. The operation is generally carried out under reflux of the reaction mixture at a temperature of between 60° and 140° C. for a period of between 10 minutes and 3 hours.

The silane of formula (V) can be run into the diester of formula (IV) and/or (IV bis) or vice versa or simultaneously.

It is preferable to employ a molar excess (from 10 to 50%) of silane of formula (V).

Operation in the presence of a catalyst is preferable, to improve the reaction kinetics. The catalysts which can be employed are those employed to carry out the hydrosilylation reaction; those which can be employed in particular are therefore organic peroxides, UV radiations and catalysts based on a metal of the platinum group, in particular platinum, ruthenium and rhodium in a proportion of 10 to 500 ppm (calculated as the weight of metal) relative to the weight of silane of formula (V).

Examples of catalysts which may be mentioned are platinum metal on carbon black, the platinum/olefin complexes described in U.S. Pat. Nos. 3,159,601 and 3,159,662, chloroplatinic acid, chloroplatinous acid, complexes of platinum with a vinylpolysiloxane which are described in U.S. Pat. No. 3,419,593, complexes of platinum of a degree close to zero which are described in U.S. Pat. Nos. 3,715,334, 3,775,452 and 3,814,730, and complexes of platinum with an organic product containing ethylenic unsaturation which are described in European Patents EP-A-188,978 and EP-A-190,530.

When the reaction has ended, the volatile products are removed by a vacuum distillation. Water pump vacuum of 0.1 to 3 kPa is generally sufficient.

During a second stage ($A_2$), the hydrolysis (or the cohydrolysis) and the polycondensation of a silane of formula (VI) are carried out.

This hydrolysis or cohydrolysis and polycondensation may be carried out preferably in an aqueous liquid phase in an acidic medium (preferably HCl) or in a basic medium (preferably $NH_4OH$) or in a solvent medium, in conditions similar to those of the hydrolysis of chlorosilanes, such as are described on pages 193 to 200 of Noll's work "Chemistry and Technology of Silicones", Academic Press (1968).

The concentration of acid or of base in the water is generally between 10 and 30% by weight. The hydrolysis medium always includes at least 2 moles of water per mole of silane, generally from 10 to 100 moles of water. The hydrolysis may be performed continuously or non-continuously at ambient temperature (20° C.) or at a temperature of between 5° and 90° C. The hydrolysis may be performed at a pressure which is equal to or higher than atmospheric pressure continuously or non-continuously with reinjection of water (at least in the case of the continuous process), to maintain a uniform aqueous phase.

The silanes of formula (VI) in which a=1 are hydrolysed and polycondensed in the optional presence of a dichlorodiorganosilane of formula:

$$R_2SiCl_2 \qquad (VII)$$

in which R has the definition given in formula (I) above, the aim being to obtain the polymers of formulae (II) and (III) or mixtures thereof.

The polycondensation may be stopped merely by neutralizing the reaction mixture. In this case, the polymers of formula (II) which are obtained are blocked by a hydroxyl (silanol) group at each of their ends, or by the $R_2ZSiO_{0.5}$ unit when the silane $R_2ZSiCl$ is employed.

The polycondensation can also be stopped by adding an organosilicon compound capable of reacting with the terminal hydroxyl groups, such as the compounds of formula:

in which the radicals R have the meaning given in formula (I) above.

The hydrolysis period may be between a few seconds and several hours.

After hydrolysis, the aqueous phase is separated from the siloxane phase by any suitable physical means, generally by phase separation and extraction with an organic solvent such as isopropyl ether.

The siloxane phase may be subsequently washed with water and then distilled if appropriate, to separate the linear polymers of formula (II) from the cyclic polymers of formula (III).

According to a second process (B) for preparing the polymers of formulae (I), (II) and (III), it is also possible to start with the corresponding polymer in which all the radicals Z and optionally Z' are hydrogen atoms and, using a hydrosilylation reaction, to add a diester of formulae (IV) and (IV bis) above.

This polymer is called polymer containing SiH in what follows; the SiH groups may be present in the chain and/or at the chain ends. These polymers containing SiH are products which are well known in the silicones industry and are generally available commercially.

They are described, for example, in U.S. Pat. Nos. 3,220,972, 3,436,366, 3,697,473 and 4,340,709.

This polymer containing SiH can therefore be denoted by the formula:

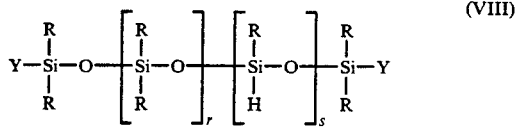

(VIII)

in which R, r and s have the meaning given above for formula (II), and the radicals Y, which are identical or different, are chosen from the radicals R and a hydrogen atom;
and the formula:

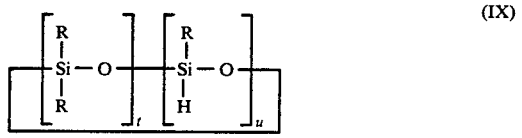

(IX)

in which R, t and u have the meaning given above for formula (III).

As in stage (A₁) of process (A), process (B) thus employs a similar hydrosilylation reaction and it is desirable that this reaction be performed with the same catalysts as those shown in stage (A₁).

This reaction can be carried out in bulk or in an organic solvent at a temperature between normal temperature (25° C.) and 170° C.

When the reaction has ended, the volatile products are removed by vacuum distillation and/or by extraction.

Process (A) makes it possible to obtain polymers of formula (II) containing hydroxyl end groups and polymers of formulae (II) and (III) containing radicals R, some of which may be vinyl radicals.

Process (B) makes it possible to have polymers of a structure which is well defined by the choice of the initial polymers containing SiH.

More especially, the compound of formula (IV) which is employed is preferably:
diesters of optionally α-methylated alkylsuccinic or methallylsuccinic acid (formula IV) in which Y is $CH_2=CH-CH_2-$ or $CH_2=C(CH_3)-CH_2-$ and X is H or $CH_3$).

The modified organopolysiloxanes obtained by the above processes (A) and (B) are also described in U.S. Pat. Nos. 4,207,246, 4,322,473 and 4,405,469, which are mentioned as references.

diesters of itaconic acid (formula IV bis); two isomeric forms of radicals Z are then obtained:

$CH_2CH(COOR')CH_2COOR'$ (formula I: W is $-CH_2-$, X is H); and $C(CH_3)(COOR')CH_2COOR'$ (formula I: W is a valency bond and X is methyl).

Diorganopolysiloxanes containing a diester functional group which are employed in accordance with the invention are generally in the form of more or less viscous oils with a viscosity of between 2 and 500,000 mPa s, preferably between 5 and 5,000 mPa s at 25° C.

Another subject of the invention consists of the cosmetic compositions for the treatment and care of hair and of the skin, containing, in a cosmetically acceptable medium a diorganopolysiloxane containing a diester functional group, including at least one unit of formula (I) per molecule in concentrations of between 0.2 and 90% and preferably between 0.3 and 60% by weight relative to the total weight of the composition.

These compositions may be presented in the form of aqueous dispersions or of oily, oleoalcoholic, alcoholic or hydroalcoholic lotions which are thickened or otherwise, and may be optionally packaged as an aerosol.

In addition to the diorganopolysiloxane containing at least one unit of formula (I) per molecule, they may also contain adjuvants which are usually employed in cosmetics, such as perfumes, colorants, oils, preserving agents, thickeners, surfactants, sequestrants, foam stabilizers, humectants, sunscreens and cosmetically active substances.

The cosmetic compositions intended for hair treatment, in accordance with the invention, may be employed in particular as shampoos, rinsing products to be applied before or after shampooing, before or after dyeing or bleaching, before or after permanent-waving or straightening, as unrinsed styling products such as in hair-setting or blow-drying lotions or, lastly, in lacquers.

When the composition forms a shampoo, it contains, in a cosmetically acceptable medium, at least one or more anionic, nonionic or amphoteric surface agents or mixtures thereof; the total concentration of surface agents being generally between 0.5 and 30% by weight and preferably between 1.5 and 15% by weight, relative to the total weight of the composition.

When the compositions are employed as rinsing products, these products may be presented in the form of aqueous dispersions or of lotions, optionally thickened, or gels.

The lotions may contain, in an aqueous medium, from 1 to 70% of a cosmetically acceptable solvent chosen more particularly from $C_1-C_4$ lower monoalcohols such as ethyl alcohol, isopropyl alcohol and tert-butyl alcohol, polyalcohols such as ethylene glycol, diethylene glycol or propylene glycol, glycol ethers such as mono- or diethylene glycol alkyl ethers, and fatty acid esters such as isopropyl myristate.

When the compositions are thickened or are presented in gel form, they contain one or more thickeners which may be chosen preferably from sodium alginate or gum arabic, cellulose derivatives such as methyl cellulose, hydroxymethyl cellulose, hydroxyethyl cellulose, hydroxypropyl cellulose, hydroxypropyl methyl cellulose or carboxymethyl cellulose, guar gum or its derivatives, xanthan gum or scleroglucans and acrylic acid polymers, crosslinked or otherwise. A thickening of the compositions can also be obtained using a mixture of polyethylene glycol and polyethylene glycol stearate or distearate or a mixture of phosphoric esters and amides.

The composition can be thickened by employing the product resulting from the ionic interaction of a cationic polymer consisting of a cellulose copolymer or of a cellulose derivative grafted with a quaternary ammonium salt of a water-soluble monomer and of a carboxylic anionic polymer which has an absolute capillary viscosity in dimethyl formamide or methanol, at a concentration of 5% and at 30° C., which is lower than or equal to $30 \times 10^{-3}$ Pa s as described more particularly in French Patent Application No. 2,598,611.

These thickeners are employed in concentrations of between 0.1 and 30% by weight and preferably between 0.2 and 15% by weight relative to the total weight of the composition.

When the compositions intended for hair treatment are employed as hair-styling or unrinsed products, they contain the diorganopolysiloxanes containing at least one unit of formula (I) per molecule in an aqueous or solvent medium, optionally in the presence of thickeners such as defined above.

The solvents are preferably chosen from $C_2$-$C_4$ lower alcohols and preferably consist of ethanol and volatile silicones such as the cyclic silicones known in the CTFA Dictionary under the designations Hexamethyldisiloxane and Cyclomethicone, and mixtures thereof.

The solvents are employed in proportions of between 5% and 99.8% by weight relative to the total weight of the composition.

The thickeners which are particularly preferred in this case are chosen from acrylic acid polymers, crosslinked or otherwise, and more particularly polyacrylic acids crosslinked with a polyfunctional agent, such as the products sold by Goodrich under the name Carbopol, cellulose derivatives such as indicated above, ethylene/maleic anhydride copolymers such as those sold by Monsanto under the name EMA 91 and copolymers of methyl vinyl ether and of maleic anhydride such as those sold by GAF under the name Gantrez AN (119, 139, 169).

The concentration of thickening agents in these compositions varies between 0.05 and 5% by weight and preferably between 0.1 and 2% by weight relative to the total weight of the composition.

The compositions in accordance with the invention may be packaged as an aerosol, to be dispensed in spray form and to form lacquers. In this case, the composition is employed in the presence of a propellent gas such as, more particularly, carbon dioxide, nitrogen, nitrous oxide, dimethyl ether, volatile hydrocarbons such as butane, iso-butane and propane, chlorinated and/or fluorinated hydrocarbons and mixtures of hydrocarbons such as n-butane, isobutane and propane with chlorofluorinated hydrocarbons.

Cosmetic compositions intended for the treatment and care of the skin may be applied in particular in the form of products for the bath or shower, body oils, suntanning products, shaving products and perfumed lotions.

These compositions contain in a cosmetically acceptable medium, suitable for application to the skin and well known to a person skilled in the art, the diorganopolysiloxanes described above, also in specified proportions.

Compositions comprising a dermatologically active substance form another subject of the invention; they contain at least one polyorganosiloxane containing a diester functional group of formula (I) in a physiologically acceptable medium, as defined above.

The cosmetic treatment process employing the diorganopolysiloxanes containing at least one unit of formula (I) per molecule, defined above, consists essentially in applying the composition either to hair in accordance with the intended use (shampoo, rinse treatment, hair-styling treatment without rinsing), or to the skin (bath, shower, and the like).

The following examples are intended to illustrate the invention without, however, being of a limiting nature.

The reference examples hereinafter are intended to illustrate the preparation of a number of compounds in accordance with the invention, while the examples of compositions illustrate the cosmetic application of these compounds.

REFERENCE EXAMPLE 1

907 g, that is 5.74 moles of methyl itaconate and 129 mg of chloroplatinic acid ($H_2PtCl_5$) are charged into a 2-liter three-necked reactor fitted with a condenser, a stirrer and a dropping funnel.

The temperature is raised to 116° C. and 792.5 g (6.89 moles) of $CH_2HSiCl_2$, that is a 20% molar excess relative to the itaconate, are then run in over 65 minutes. Since the reaction is exothermic, the temperature stays in the region of 120° C. without additional heat input. At the end of the addition the temperature is 112° C. The reaction mixture is kept under reflux for 1 hour 50 minutes and the excess $CH_3HSiCl_2$ is then distilled off and 1274 g of liquid adduct are obtained, whose boiling point is 80° C. at 0.13 kPa. The weight yield of adduct is 71%.

NMR analysis of the adduct shows that it contains approximately 60 mole % of radicals —($CH_2$)—CH—(-COOCH_3)—$CH_2$—COOCH_3 and 40 mole % of unit —C($CH_3$)—(COOCH_3)—$CH_2$—COOCH_3.

REFERENCE EXAMPLE 2

Preparation of a compound of formula (II) in which:
One of the radicals R denotes $CH_3$, the two end radicals denote OH;
Z, equal to Z', is a mixture of radicals
—$CH_2$—CH—(COOCH_3)—$CH_2$—COOCH_3 and
—C($CH_3$)—(COOCH_3)—$CH_2$—COOCH_3;
r has the value 0;
s represents an average statistical value equal to 6.6.

340 g of an aqueous ammonia solution ($NH_4OH$ at a concentration of 20% by weight) and 370 ml of water are charged into the same three-necked reactor as that employed in Reference Example 1. 500 g (1.83 moles) of the adduct obtained in Example 1, in solution in 500 ml of isopropyl ether, are run in over 50 minutes, the temperature being maintained at 25° C.

When hydrolysis has ended, the mother liquors are separated off and 500 ml of isopropyl ether are again added to promote phase separation. The organic solution separated off is washed again with water, is dried and is devolatilized up to a temperature of 100° C. under a vacuum of 2 kPa.

323 g of a clear oil are then obtained, with a hydroxyl group weight content of 1.8%, a viscosity of 35 mPa s at 25° C. and a weight percentage of ester functional group of 54.2%.

REFERENCE EXAMPLE 3

Preparation of a compound of formula (II) in which:
R denotes $CH_3$;
Z' denotes OH;
Z is a mixture of radicals:
—$CH_2$—CH—(COOCH$_3$)—$CH_2$—COOCH$_3$ and
—C(CH$_3$)—(COOCH$_3$)—$CH_2$—COOCH$_3$;
r denotes a means statistical value equal to 40;
s denotes a mean statistical value equal to 2.

2800 g of water are charged into a 10-liter three-necked reactor and onto it are run in over one hour 903 g (7 moles) of $(CH_3)_2SiCl_2$ and 98 g (0.35 moles) of the adduct obtained in Example 1. During the addition, the temperature rises gradually from 25° to 65° C. After the addition the reaction mixture is kept stirred for 30 minutes and the acidic water is separated off. 350 ml of isopropyl ether are added, three washings are performed, and the ether solution is concentrated, firstly up to 100° C. at atmospheric pressure and then up to 80° C. under a vacuum of 2.5 kPa.

456 g of a clear and colourless oil are then obtained, having the following characteristics:

| | |
|---|---|
| Viscosity at 25° C. | 20 mPa s |
| % (by weight) of hydroxyl | 1% |
| & (by weight) of ester functional group | 4.8% |
| Weight yield of oil | 77% |

REFERENCE EXAMPLE 4

Preparation of a compound of formula (II) in which:
Z' is identical with R and denotes $CH_2$;
Z is a mixture of radicals:
—$CH_2$—CH—(COOCH$_3$)—$CH_2$—COOCH$_3$ and
—C(CH$_3$)—(COOCH$_3$)—$CH_2$—COOCH$_3$.
r has the value 31;
s has the value 17.

The following are charged into a 5-liter three-necked reactor: 816 g of an oil of formula:

$(CH_3)_3SiO(CH_3HSiO)_{17}[(CH_3)_2(SiO)]_{31}Si(CH_3)_3$ and 948 g of methyl itaconate, the whole in 1540 g of xylene, together with chloroplatinic acid in a quantity such that there are approximately 150 ppm of platinum metal relative to the weight of siloxane polymer. The temperature is raised to 145° C. and is maintained thereat for 24 hours. Xylene and excess methyl itaconate are then distilled off by heating to 140° C. under a vacuum of 2.5 kPa.

1370 g of a clear and colourless oil are then obtained, with a viscosity of 950 mPa s at 25° C. and a percentage by weight of ester functional group of 28.2%.

REFERENCE EXAMPLE 5

Preparation of a compound of formula (III).

The following are charged at the same time into a 1-liter reactor fitted with a condenser and a stirrer:
174 g, that is 1.1 mole of methyl itaconate;
46 g of a cyclic hydromethylsiloxane of 92% purity, of formula:

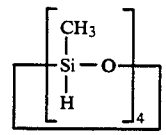

25 mg of $H_2PtCl_6(6H_2O)$.

The reaction mixture is heated to 135° C. and the temperature is maintained between 135° and 160° C. for 1 hour 30 minutes.

The excess methyl itaconate is distilled out of the reaction mixture at 160° C. at 0.133 kPa. 146 g of devolatilized oil are obtained of orangy yellow colour, with a viscosity of 2240 mPa s at 25° C., in which the weight percentage of ester is 50%.

The mass spectrum and the IR spectrum (CHCl$_3$) confirm that the oil obtained is indeed the product:

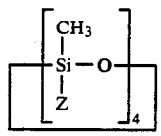

Z being an itaconyl radical.

EXAMPLE 1

A spray of the following composition is prepared:

| | |
|---|---|
| diorganopolysiloxane containing a dimethyl itaconate functional group of Reference Example 3 | 4 g |
| Perfume q.s. | |
| Absolute ethyl alcohol q.s. | 100 g |

The composition is packaged in a pump bottle. When applied to dried hair, this spray makes it shine. In particular, it restores shine to hair dulled by chemical bleaching or permanent-wave treatments or by atmospheric attack, without making it greasy.

EXAMPLE 2

A spray of the following composition is prepared:

| | |
|---|---|
| Diorganopolysiloxane containing a dimethyl itaconate functional group Reference Example 4 | 3 g |
| Perfume q.s. | |
| Absolute ethyl alcohol q.s. | 100 g |

The composition is packaged in a pump bottle. As in Example 1, this spray makes the hair shine without making it greasy.

EXAMPLE 3

A hair-care composition is prepared, for application to dried hair:

| | |
|---|---|
| Diorganopolysiloxane containing a dimethyl itaconate functional group of Reference Example 3 | 50 g |
| Chain- end hydroxylated polydimethylsiloxane of MW 500,000 as a 13% solution in a cyclic polydimethylsiloxane (87%), sold by Dow Corning under the name | 50 g |

| | |
|---|---|
| Q2 1401 | |

This care product makes the hair soft, shiny and smooth.

EXAMPLE 4

A care composition is prepared, for application to dried hair:

| | |
|---|---|
| Diorganopolysiloxane containing a dimethyl itaconate functional group of Reference Example | 450 g |
| 2-Ethylhexyl p-methoxycinnamate (Parsol MCX) | 1 g |
| 2-Ethylhexyl dimethyl-p-aminobenzoate (Padimate O) | 1 g |
| Cyclic dimethylpolysiloxane sold by Union Carbide under the name Volatile Silicone 7158 | 15 g |
| Cyclic dimethylpolysiloxane sold by Union Carbide under the name Volatile Silicone 7207 | 15 g |
| Perfume, preserving agent q.s. | |
| Absolute ethyl alcohol q.s. | 100 g |

This composition, which is very easy to apply, makes the hair soft, supple and shiny without giving it a greasy feel.

EXAMPLE 5

A styling gel is prepared, of the following composition:

| | |
|---|---|
| Diorganopolysiloxane containing a dimethyl itaconate functional group of Reference Example 3 | 20 g |
| crosslinked polyacrylic acid, MW: 4,000,000 sold by Goodrich under the name Carbopol 940, neutralized with NH$_4$OH | 1 g |
| Perfume q.s. | |
| Water q.s. | 100 g |

When applied to dry hair, this gel makes the hair style easier to maintain and improves the softness and the shine without imparting a greasy feel.

EXAMPLE 6

A shampoo of the following composition is prepared:

| | |
|---|---|
| Diorganopolysiloxane containing a dimethyl itaconate functional group of Reference Example 2 | 5 g |
| Amphoteric surfactant called Cocoamphocarboxyglycinate in the CTFA Dictionary (3rd edition) 1982, sold by Miranol at a concentration of 38% of active substance (AS) under the name of Miranol C$_2$M | 7 g AS |
| Polyglycolic ether carboxylic acid of formula: R(OCH$_2$CH$_2$)$_4$OCH$_2$COOH where R = mixture of C$_{12}$H$_{25}$ and C$_{14}$H$_{29}$ radicals, sold at a concentration of 90% of active substance (AS) by Chem-Y under the name Akypo RLM 45 | 2.5 g AS |
| Oxyethylenated polydimethylsiloxane containing 70% of ethylene oxide, sold by Dow Corning under the name Dow Corning 193 | 6.5 g |
| HCl q.s. pH = 4.5 | |
| Water | 100 g |

When washed with this shampoo, the hair is soft, supple and free from a greasy feel.

EXAMPLE 7

A shampoo of the following composition is prepared:

| | |
|---|---|
| Diorganopolysiloxane containing a dimethyl itaconate functional group of Reference Example 3 | 0.4 g |
| (C$_{12}$-C$_{18}$ Alkyl) dimethylcarboxymethyl-ammonium hydroxide, sold at a concentration of 30% of active substance (AS) by Henkel under the name Dehyton AB 30 | 10 g AS |
| Preserving agent, perfume q.s. | |
| Water q.s. | 100 g |

This shampoo, with good foaming properties, makes the hair easy to disentangle, shiny and soft.

EXAMPLE 8

An oil of the following composition, to be applied, for example, after the bath, is prepared:

| | |
|---|---|
| Diorganopolysiloxane containing a dimethyl itaconate functional group of Reference Example 3 | 40 g |
| Rapeseed oil | 13.3 g |
| Liquid petrolatum | 6.7 g |
| Decamethylcyclopentasiloxane q.s. | 100.0 g |

This oil imparts suppleness and softness to the skin.

We claim:

1. A cosmetic or dermatological composition which contains in a cosmetically or physiologically acceptable medium, at least one diorganopolysiloxane containing a diester functional group, carrying, per molecule at least one unit of formula:

$$ZR_aSiO_{(3-a)/2} \qquad (I)$$

in which:
 a is 0, 1 or 2
 Z denotes a radical of formula:

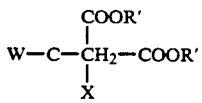

in which:
 the symbols R', which are identical or different, denote a C$_1$-C$_{12}$ monovalent saturated hydrocarbon radical, a C$_2$-C$_{12}$ monovalent alkoxyalkyl radical, or a C$_6$-C$_{12}$ aryl, alkylaryl or aralkyl radical;
 X denotes a hydrogen atom or a methyl radical;
 W denotes a covalent bond or a C$_1$-C$_4$ linear or branched alkylene radical;
 the symbols R, which are identical or different, denote a C$_1$-C$_{20}$ alkyl, vinyl, phenyl, 3,3,3-trifluoropropyl or hydroxyl radical, provided that only one radical R per silicon atom may be a hydroxyl group; and mixtures thereof.

2. A composition according to claim 1, wherein the diorganopolysiloxane containing a diester functional group also carries other siloxyl units corresponding to the formula:

$$R_b SiO_{(4-b)/2} \quad \text{(I bis)}$$

in which:
R has the same meanings as above and b is equal to 0, 1, 2 or 3.

3. A composition according to claim 1 wherein the diorganopolysiloxanes carrying at least one unit of formula (I) per molecule the $C_1$-$C_{12}$ alkyl groups denoted by R' are chosen from methyl, ethyl, n-propyl, isopropyl, n-butyl, 2-ethylhexyl, heptyl and dodecyl radicals, the $C_4$-$C_{12}$ aryl, aralkyl and alkylaryl radicals are chosen from phenyl, benzyl and tolyl, the $C_2$-$C_{12}$ alkoxyalkyl radicals are chosen from methoxymethyl, ethoxymethyl and 2-methoxyethyl radicals, the radical W denotes alkylene radicals chosen from:

$$-CH_2-, \ -(CH_2)_3-, \ -CH_2-\underset{\underset{CH_3}{|}}{CH}-CH_2-$$

when X denotes a hydrogen or else W is a covalent bond when X is a methyl group;
R denotes a methyl, ethyl, propyl, n-butyl, n-octyle or 2-ethylhexyl radical.

4. A composition according to claim 1 wherein 80% of the number of the radicals R in the diorganopolysiloxanes carrying at least one unit of formula (I) per molecule are methyl radicals.

5. A composition according to claim 1 wherein the diorganopolysiloxanes are chosen from:
(i) the compounds corresponding to the formula:

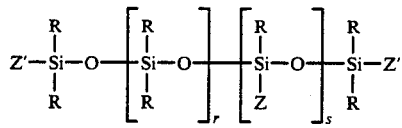

in which:
R has the meaning defined in claim 1;
the symbols Z', which are identical or different, are chosen from Z and R;
Z is chosen from the radicals
—CH$_2$—CH—(COOR')CH$_2$COOR'
—C(CH$_3$) (COOR')CH$_2$COOR'
R' having the meaning defined in claim 1;
r is an integer between 0 and 500 inclusive;
s is an integer chosen between 0 and 50 inclusive; and if s is equal to 0, one of the symbols Z' denotes Z;
(ii) the cyclic polysiloxanes of formula:

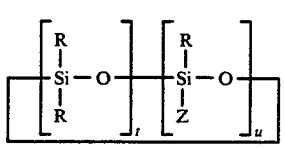

in which;
R and Z have the meaning defined above;
u is an integer between 1 and 20 inclusive;
t is an integer between 0 and 20 inclusive;
t+u is greater than or equal to 3.

6. A composition according to claim 1, wherein the diorganopolysiloxanes are random or block polymers exhibiting one of the following characteristics:
a) R and R' are methyl
b) r is between 5 and 50 inclusive
c) s is between 1 and 20 inclusive
d) t+u is between 3 and 10 inclusive.

7. Composition according to claim 1 which is presented in the form of aqueous dispersions or of oily, oleoalcoholic, alcoholic or hydroalcoholic lotions, thickened or otherwise, optionally packaged as an aerosol.

8. Composition according to claim 1 containing one or more adjuvants from selected from the group consisting of perfumes, colorants, oils, preserving agents, thickeners, anionic, nonionic or amphoteric surface-active agents or mixtures thereof, sequestrants, foam stabilizers, humectants, and sunscreens.

9. Composition according to claim 1 in the form of a shampoo, which additionally contains at least one or more anionic, nonionic or amphoteric surface agents or mixtures thereof, in proportions of between 0.5 and 30% by weight relative to the total weight of the composition.

10. Composition according to claim 1, which contains at least 1 to 70% of solvent chosen from lower alkanols, polyalcohols, glycol ethers and fatty acid esters.

11. Composition according to claim 1 which is thickened or gelled with an agent chosen from sodium alginate, gum arabic, cellulose derivatives, guar gum, xanthan gum and scleroglucans, acrylic acid polymers, crosslinked or otherwise, a mixture of polyethylene glycol and of polyethylene glycol stearate or distearate, a mixture of phosphoric ester and of amide, the product of ionic interaction between a cationic polymer consisting of a cellulose copolymer or a cellulose derivative grafted with a quaternary ammonium salt of a water-soluble monomer and a carboxylic anionic polymer which has an absolute capillary viscosity lower than or equal to $30 \times 10^{-3}$ Pa s in dimethyl formamide or methanol at a concentration of 5% and at 30° C.; this thickening agent is present in proportions of between 0.1 and 30% by weight relative to the total weight of the composition.

12. Composition for cosmetic treatment of hair or of the skin, characterized in that it contains, in a cosmetically acceptable medium, at least one diorganopolysiloxane containing a diester functional group, carrying per molecule at least one unit of formula:

$$ZR_a SiO_{(3-a)/2} \quad \text{(I)}$$

in which:
a is 0, 1 or 2
Z denotes a radical of formula:

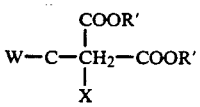

in which:
the symbols R', which are identical or different, denote a $C_1$-$C_{12}$ monovalent saturated hydrocarbon radical, a $C_2$-$C_{12}$ monovalent alkoxyalkyl radical, or a $C_6$-$C_{12}$ aryl, alkylaryl or aralkyl radical;
X denotes a hydrogen atom or a methyl radical;

W denotes a covalent bond or a $C_1$-$C_4$ linear or branched alkylene radical;

the symbols R, which are identical or different, denote a $C_1$-$C_{20}$ alkyl, vinyl, phenyl, 3,3,3-trifluoropropyl or hydroxyl radical, provided that only one radical R per silicon atom may be a hydroxyl group; and mixtures thereof, in concentrations of between 0.2 and 90% by weight.

13. Composition according to claim 12 in the form of a hair-styling product for use without rinsing, a hair-setting or blow-drying lotion or a lacquer, which contain an aqueous or solvent medium, the solvents being chosen from $C_2$-$C_4$ lower alkanols and volatile silicones.

14. Dermatological composition comprising a dermatological active substance characterized in that it contains, in a physiologically acceptable medium, at least one diorganopolysiloxane containing a diester functional group carrying per molecule at least one unit of formula I in accordance with claim 1.

15. Composition according to claim 13, which contains thickeners chosen from acrylic acid polymers, crosslinked or otherwise, cellulose derivatives, ethylene/maleic anhydride copolymers and copolymers of methyl vinyl ether and of maleic anhydride, in proportions of between 0.05 and 5% by weight.

16. Composition according to claim 12 which is packaged as an aerosol to form a spray at the time of expulsion, in the presence of a propellent gas.

17. Composition according to claim 12 which contains said diorganopolysiloxane in concentrations of between 0.3 and 60% by weight relative to the total weight of the composition.

18. Composition according to claim 12 in the form of a rinsing product for application before or after shampooing, before or after dyeing or bleaching, before or after permanent waving or straightening, which is presented in the form of an aqueous dispersion, lotion, thickened lotion or gel.

19. Composition according to claim 12 for the treatment and care of the skin which is applied in the form of a bath or shower product; a body oil; a sun-tanning product; a shaving product or a perfume lotion.

20. Process for a cosmetic treatment of hair, which comprises applying thereto at least one composition which contains, in a cosmetically or physiologically acceptable medium, at least one diorganopolysiloxane containing a diester functional group, carrying, per molecule, at least one unit of formula:

$$ZR_aSiO_{(3-a)/2} \qquad (I)$$

in which:

a is 0, 1 or 2

Z denotes a radical of formula:

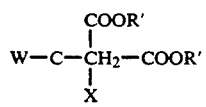

in which:

the symbols R', which are identical or different, denote a $C_1$-$C_{12}$ monovalent saturated hydrocarbon radical, a $C_2$-$C_{12}$ monovalent alkoxyalkyl radical, or a $C_6$-$C_{12}$ aryl, alkylaryl or aralkyl radical;

X denotes a hydrogen atom or a methyl radical;

W denotes a covalent bond or a $C_1$-$C_4$ linear or branched alkylene radical;

the symbols R, which are identical or different, denote a $C_1$-$C_{20}$ alkyl, vinyl, phenyl, 3,3,3-trifluoropropyl or hydroxyl radical provided that only one radical R per silicon atom may be a hydroxyl group; and mixtures thereof, in concentrations of between 0.2 and 90% by weight.

21. Process for a cosmetic treatment of the skin, which comprises applying thereto at least one composition which contains, in a cosmetically or physiologically acceptable medium, at least one diorganopolysiloxane containing a diester functional group, carrying, per molecule, at least one unit of formula:

$$ZR_aSiO_{(3-a)/2} \qquad (I)$$

in which:

a is 0, 1 or 2

Z denotes a radical of formula:

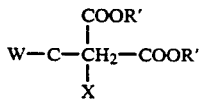

in which:

the symbols R', which are identical or different, denote a $C_1$-$C_{12}$ monovalent saturated hydrocarbon radical, a $C_2$-$C_{12}$ monovalent alkoxyalkyl radical, or a $C_6$-$C_{12}$ aryl, alkylaryl or aralkyl radical;

X denotes a hydrogen atom or a methyl radical;

W denotes a covalent bond or a $C_1$-$C_4$ linear or branched alkylene radical;

the symbols R, which are identical or different, denote a $C_1$-$C_{20}$ alkyl, vinyl, phenyl, 3,3,3-trifluoropropyl or hydroxyl radical, provided that only one radical R per silicon atom may be a hydroxyl group; and mixtures thereof, in concentration between 0.2 and 90% by weight.

* * * * *